(12) United States Patent
Huang et al.

(10) Patent No.: US 9,329,306 B2
(45) Date of Patent: May 3, 2016

(54) CARBOSILOXANE VINYLIC MONOMERS

(71) Applicant: Novartis AG, Basel (CH)

(72) Inventors: Jinyu Huang, Suwanee, GA (US); Frank Chang, Cumming, GA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/694,590

(22) Filed: Apr. 23, 2015

(65) Prior Publication Data
US 2015/0309211 A1 Oct. 29, 2015

Related U.S. Application Data

(60) Provisional application No. 61/984,101, filed on Apr. 25, 2014.

(51) Int. Cl.
| | | |
|---|---|---|
| *C08F 230/08* | (2006.01) | |
| *C08F 30/08* | (2006.01) | |
| *C08L 83/04* | (2006.01) | |
| *G02B 1/04* | (2006.01) | |
| *C07F 7/18* | (2006.01) | |
| *C07F 7/08* | (2006.01) | |

(52) U.S. Cl.
CPC .............. *G02B 1/043* (2013.01); *C07F 7/0852* (2013.01); *C07F 7/0854* (2013.01); *C07F 7/1844* (2013.01); *C08F 30/08* (2013.01); *C08F 230/08* (2013.01); *C08L 83/04* (2013.01)

(58) Field of Classification Search
None
See application file for complete search history.

(56) References Cited

U.S. PATENT DOCUMENTS

| | | |
|---|---|---|
| 4,136,250 A | 1/1979 | Mueller |
| 4,153,641 A | 5/1979 | Deichert |
| 4,182,822 A | 1/1980 | Chang |
| 4,189,546 A | 2/1980 | Deichert |
| 4,254,248 A | 3/1981 | Friends |
| 4,259,467 A | 3/1981 | Keogh |
| 4,260,725 A | 4/1981 | Keogh |
| 4,261,875 A | 4/1981 | LeBoeuf |
| 4,276,402 A | 6/1981 | Chromecek |
| 4,327,203 A | 4/1982 | Deichert |
| 4,341,889 A | 7/1982 | Deichert |
| 4,343,927 A | 8/1982 | Chang |
| 4,355,147 A | 10/1982 | Deichert |
| 4,444,711 A | 4/1984 | Schad |
| 4,460,534 A | 7/1984 | Boehm |
| 4,486,577 A | 12/1984 | Mueller |
| 4,543,398 A | 9/1985 | Bany |
| 4,605,712 A | 8/1986 | Mueller |
| 4,661,575 A | 4/1987 | Tom |
| 4,684,538 A | 8/1987 | Klemarczyk |
| 4,703,097 A | 10/1987 | Wingler |
| 4,833,218 A | 5/1989 | Lee |
| 4,837,289 A | 6/1989 | Mueller |
| 4,954,586 A | 9/1990 | Toyoshima |
| 4,954,587 A | 9/1990 | Mueller |
| 5,010,141 A | 4/1991 | Mueller |
| 5,034,461 A | 7/1991 | Lai |
| 5,039,761 A | 8/1991 | Ono |
| 5,070,170 A | 12/1991 | Robertson |
| 5,079,319 A | 1/1992 | Mueller |
| 5,247,046 A | 9/1993 | Takago |
| 5,346,946 A | 9/1994 | Yokoyama |
| 5,358,995 A | 10/1994 | Lai |
| 5,387,632 A | 2/1995 | Lai |
| 5,416,132 A | 5/1995 | Yokoyama |
| 5,451,617 A | 9/1995 | Lai |
| 5,484,868 A | 1/1996 | Kobayashi |
| 5,486,579 A | 1/1996 | Lai |
| 5,527,925 A | 6/1996 | Chabrecek |
| 5,583,163 A | 12/1996 | Muller |
| 5,612,389 A | 3/1997 | Chabrecek |
| 5,612,391 A | 3/1997 | Chabrecek |
| 5,621,018 A | 4/1997 | Chabrecek |
| 5,665,840 A | 9/1997 | Pohlmann |
| 5,712,356 A | 1/1998 | Bothe |
| 5,760,100 A | 6/1998 | Nicolson |
| 5,843,346 A | 12/1998 | Morrill |
| 5,849,841 A | 12/1998 | Mühlebach |
| 5,894,002 A | 4/1999 | Boneberger |
| 5,936,052 A | 8/1999 | Bothe |
| 5,962,548 A | 10/1999 | Vanderlaan |
| 5,981,675 A | 11/1999 | Valint, Jr. |
| 5,998,498 A | 12/1999 | Vanderlaan |
| 6,039,913 A | 3/2000 | Hirt |
| 6,043,328 A | 3/2000 | Domschke |
| 6,165,408 A | 12/2000 | Steinmann |
| 6,221,303 B1 | 4/2001 | Steinmann |
| 6,291,021 B1 | 9/2001 | Morita |
| 6,303,687 B1 | 10/2001 | Müller |
| 6,342,570 B1 | 1/2002 | Bothe |
| 6,420,504 B1 | 7/2002 | Yoshitake |
| 6,472,489 B1 | 10/2002 | Stockinger |
| 6,479,587 B1 | 11/2002 | Stockinger |
| 6,492,478 B1 | 12/2002 | Steinmann |
| 6,534,590 B1 * | 3/2003 | Aso ........................ C08F 230/08 106/287.16 |

(Continued)

FOREIGN PATENT DOCUMENTS

| | | |
|---|---|---|
| EP | 961941 B1 | 4/2001 |
| EP | 958315 B1 | 6/2001 |

(Continued)

OTHER PUBLICATIONS

STIC structure search, Dec. 8, 2015, 14694590-501379-EICSEARCH.*

(Continued)

*Primary Examiner* — Peter A Salamon
(74) *Attorney, Agent, or Firm* — Jian Zhou

(57) ABSTRACT

The invention provides a carbosiloxane vinylic monomer which comprises one sole ethylenically unsaturated group, one sole terminal butyl group; and one oligo(carbosiloxane)-containing linkage between the ethylenically unsaturated terminal group and the terminal butyl group. The present invention is also related to a polymer, an actinically-crosslinkable silicone-containing prepolymer, a silicone hydrogel polymeric material, or a silicone hydrogel contact lens, which comprises monomeric units derived from a carbosiloxane vinylic monomer of the invention.

12 Claims, No Drawings

(56) References Cited

U.S. PATENT DOCUMENTS

| | | |
|---|---|---|
| 6,627,124 B1 | 9/2003 | Herbrechtsmeier |
| 6,762,264 B2 | 7/2004 | Kuenzler |
| 6,800,225 B1 | 10/2004 | Hagmann |
| 7,091,283 B2 | 8/2006 | Müller |
| 7,214,809 B2 | 5/2007 | Zanini |
| 7,238,750 B2 | 7/2007 | Müller |
| 7,259,220 B1 | 8/2007 | Farris |
| 7,268,189 B2 | 9/2007 | Müller |
| 7,384,590 B2 | 6/2008 | Kelly |
| 7,387,759 B2 | 6/2008 | Kelly |
| 7,396,890 B2 | 7/2008 | Zanini |
| 7,507,775 B2 | 3/2009 | Leatherman |
| 7,521,519 B1 | 4/2009 | Hirt |
| 7,566,754 B2 | 7/2009 | Müller |
| 7,605,190 B2 | 10/2009 | Moszner |
| 7,700,797 B2 | 4/2010 | Leatherman |
| 7,838,698 B2 | 11/2010 | Fujisawa |
| 7,915,323 B2 * | 3/2011 | Awasthi ............ C08F 30/08 523/106 |
| 7,956,135 B2 | 6/2011 | Hirt |
| 8,044,111 B2 | 10/2011 | Chang |
| 8,048,968 B2 | 11/2011 | Phelan |
| 8,071,658 B2 | 12/2011 | Zhou |
| 8,071,696 B2 | 12/2011 | Hirt |
| 8,071,703 B2 | 12/2011 | Zhou |
| 8,211,955 B2 | 7/2012 | Chang |
| 8,263,679 B2 | 9/2012 | Zhou |
| 8,283,429 B2 | 10/2012 | Zhou |
| 8,404,783 B2 | 3/2013 | Chang |
| 8,420,711 B2 * | 4/2013 | Awasthi ............ C08F 226/08 523/107 |
| 8,524,800 B2 | 9/2013 | Phelan |
| 8,541,009 B2 * | 9/2013 | Iida .................. A61K 8/375 424/401 |
| 2005/0008597 A1 * | 1/2005 | Furukawa ........... A61K 8/046 424/70.12 |
| 2005/0113549 A1 | 5/2005 | Devlin |
| 2007/0207443 A1 * | 9/2007 | Eckert ............... A61K 6/0005 433/217.1 |
| 2008/0003195 A1 * | 1/2008 | Arnaud ............... A61K 8/90 424/78.03 |
| 2008/0015315 A1 | 1/2008 | Chang |
| 2008/0143003 A1 | 6/2008 | Phelan |
| 2008/0143958 A1 | 6/2008 | Medina |
| 2008/0231798 A1 | 9/2008 | Zhou |
| 2008/0234457 A1 | 9/2008 | Zhou |
| 2010/0120939 A1 | 5/2010 | Phelan |
| 2010/0296049 A1 | 11/2010 | Justynska |
| 2010/0298446 A1 | 11/2010 | Chang |
| 2011/0009658 A1 * | 1/2011 | Awasthi ............ C07F 7/0852 556/419 |
| 2011/0063567 A1 | 3/2011 | Domschke |
| 2011/0117041 A1 * | 5/2011 | Chantal .............. A61K 8/375 424/64 |
| 2012/0029111 A1 | 2/2012 | Chang |
| 2012/0088843 A1 | 4/2012 | Chang |
| 2012/0088844 A1 | 4/2012 | Kuyu |
| 2012/0088861 A1 | 4/2012 | Huang |
| 2012/0244088 A1 * | 9/2012 | Saxena ............... A61K 47/34 424/49 |
| 2012/0245249 A1 * | 9/2012 | Saxena ............... C08L 43/04 523/122 |
| 2012/0251605 A1 * | 10/2012 | Iimura .............. A61K 8/0241 424/401 |
| 2012/0263662 A1 * | 10/2012 | Iimura .............. A61K 8/891 424/59 |
| 2013/0142743 A1 * | 6/2013 | Cavazzuti ........... A61K 8/8194 424/64 |
| 2015/0320647 A1 * | 11/2015 | Shirai ................ A61Q 1/10 424/69 |

FOREIGN PATENT DOCUMENTS

| | | |
|---|---|---|
| EP | 932635 B1 | 7/2001 |
| WO | 00/31150 A1 | 6/2000 |
| WO | 2012/078457 A1 | 6/2012 |

OTHER PUBLICATIONS

PCT International Search Report dated Jul. 2, 2015, International Application No. PCT/US2015/027335, International Filing Date Apr. 23, 2015.

PCT Written Opinion of the International Searching Authority dated Jul. 2, 2015, International Application No. PCT/US2015/027335, International Filing Date Apr. 23, 2015.

\* cited by examiner

CARBOSILOXANE VINYLIC MONOMERS

This application claims the benefits under 35 USC §119 (e) of U.S. provisional application No. 61/984,101 filed 25 Apr. 2014, incorporated by reference in its entirety.

The present invention is related to carbosiloxane vinylic monomers useful for making silicone hydrogel ophthalmic lenses (in particular contact lenses) having relatively-long thermal stability and to such ophthalmic lenses (in particular contact lenses).

BACKGROUND

In recent years, soft silicone hydrogel contact lenses become more and more popular because of their high oxygen permeability and comfort. "Soft" contact lenses can conform closely to the shape of the eye, so oxygen cannot easily circumvent the lens. Soft contact lenses must allow oxygen from the surrounding air (i.e., oxygen) to reach the cornea because the cornea does not receive oxygen from the blood supply like other tissue. If sufficient oxygen does not reach the cornea, corneal swelling occurs. Extended periods of oxygen deprivation cause the undesirable growth of blood vessels in the cornea. By having high oxygen permeability, a silicone hydrogel contact lens allows sufficient oxygen permeate through the lens to the cornea and to have minimal adverse effects on corneal health.

Typically, silicone hydrogel contact lenses are produced according to a cast molding technique involving use of disposable or reusable molds and a silicone hydrogel lens formulation (i.e., a mixture of vinylic monomers and/or vinylic macromers). A silicone hydrogel lens formulation often comprises a siloxane-containing vinylic monomer having a tris (trialkylsilyloxy)silylalkyl group (e.g., tris(trimethylsilyloxy)-silylpropyl acrylate, tris(trimethylsilyloxy)-silylpropyl methacrylate, tris(trimethylsilyloxy)-silylpropyl acryalmide, tris(trimethylsilyloxy)-silylpropyl methacrylamide, tris-(trimethylsiloxysilyl) propylvinyl carbamate, etc.), one or more hydrophilic vinylic monomers (e.g., N,N-dimethylacrylamide, N-vinyl pyrrolidone, hydroxyethylmethacrylate, N-vinylacetamide, N-methyl-3-methylene-2-pyrrolidone, or mixtures thereof), and one or more polysiloxane vinylic monomers/macromers. It is believed that such a tris(trialkylsilyloxy)silylalkyl-containing vinylic monomer can provide resultant silicone hydrogel contact lenses with good optical properties and a high oxygen permeability. However, silicone hydrogel lenses produced from a lens formulation comprising a tris(trialkylsilyloxy)silylalkyl-containing vinylic monomer may not have a desired thermal stability when being stored in an aqueous solution, because monomeric units derived from the tris(trialkylsilyloxy)silylalkyl-containing vinylic monomer are susceptible to hydrolysis.

Therefore, there is still a need for hydrolytically-stable silicone-containing vinylic monomers suitable for making silicone hydrogel contact lenses with long thermal stability.

SUMMARY OF THE INVENTION

In one aspect, the invention provides a carbosiloxane vinylic monomer having one sole actinically polymerizable terminal group and one terminal butyl group.

The present invention, in another aspect, provides a polymer comprising monomeric units derived in a free radical polymerization from a carbosiloxane vinylic monomer of the invention.

The present invention, in a further aspect, provides a silicone hydrogel contact lens comprising monomeric units derived from a carbosiloxane vinylic monomer of the invention.

DETAILED DESCRIPTION OF EMBODIMENTS OF THE INVENTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art.

"About" as used herein means that a number referred to as "about" comprises the recited number plus or minus 1-10% of that recited number.

An "ophthalmic device", as used herein, refers to a contact lens (hard or soft), an intraocular lens, a corneal onlay, other ophthalmic devices (e.g., stents, glaucoma shunt, or the like) used on or about the eye or ocular vicinity.

"Contact Lens" refers to a structure that can be placed on or within a wearer's eye. A contact lens can correct, improve, or alter a user's eyesight, but that need not be the case. A contact lens can be of any appropriate material known in the art or later developed, and can be a soft lens, a hard lens, or a hybrid lens. A "silicone hydrogel contact lens" refers to a contact lens comprising a silicone hydrogel material.

A "hydrogel" or "hydrogel material" refers to a crosslinked polymeric material which is insoluble in water, but can absorb at least 10 percent by weight of water when it is fully hydrated.

A "silicone hydrogel" refers to a silicone-containing hydrogel obtained by copolymerization of a polymerizable composition comprising at least one silicone-containing monomer or at least one silicone-containing macromer or at least one crosslinkable silicone-containing prepolymer.

"Hydrophilic," as used herein, describes a material or portion thereof that will more readily associate with water than with lipids.

A "vinylic monomer" refers to a compound that has one sole ethylenically unsaturated group and is soluble in a solvent.

The term "soluble", in reference to a compound or material in a solvent, means that the compound or material can be dissolved in the solvent to give a solution with a concentration of at least about 0.5% by weight at room temperature (i.e., a temperature of about 20° C. to about 30° C.).

The term "insoluble", in reference to a compound or material in a solvent, means that the compound or material can be dissolved in the solvent to give a solution with a concentration of less than 0.005% by weight at room temperature (as defined above).

As used in this application, the term "ethylenically unsaturated group" is employed herein in a broad sense and is intended to encompass any groups containing at least one >C=C< group. Exemplary ethylenically unsaturated groups include without limitation (meth)acryloyl

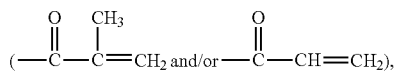

allyl, vinyl, styrenyl, or other C=C containing groups.

The term "ene group" refers to a monovalent radical comprising $CH_2=CH—$ that is not covalently attached to an oxygen or nitrogen atom or a carbonyl group.

As used herein, "actinically" in reference to curing, crosslinking or polymerizing of a polymerizable composition, a prepolymer or a material means that the curing (e.g., crosslinked and/or polymerized) is performed by actinic irradiation, such as, for example, UV irradiation, ionizing radiation (e.g. gamma ray or X-ray irradiation), microwave irradiation, and the like. Thermal curing or actinic curing methods are well-known to a person skilled in the art.

As used in this application, the term "hydrophilic vinylic monomer" refers to a vinylic monomer capable of forming a homopolymer that is water-soluble or can absorb at least 10 percent by weight water at room temperature.

As used in this application, the term "hydrophobic vinylic monomer" refers to a vinylic monomer which as a homopolymer typically yields a polymer that is insoluble in water and can absorb less than 10 percent by weight water at room temperature.

A "macromer" or "prepolymer" refers to a compound or a starting polymer that has a weight average molecular weight of greater than 700 Daltons and contains two or more ethylenically unsaturated groups and can be cured (e.g., crosslinked) actinically or thermally to obtain a crosslinked polymer having a weight average molecular weight much higher than the compound or the starting polymer.

A "polymer" means a material formed by polymerizing/crosslinking one or more vinylic monomers, macromers and/or prepolymers.

"Molecular weight" of a polymeric material (including monomeric or macromeric materials), as used herein, refers to the weight average molecular weight unless otherwise specifically noted or unless testing conditions indicate otherwise.

As used in this application, the term "crosslinker" refers to a compound or polymer having at least two ethylenically unsaturated groups and being soluble in a solvent at room temperature. A "crosslinking agent" refers to a crosslinker having a molecular weight of about 700 Daltons or less.

A "polysiloxane" refers to a compound containing one sole polysiloxane segment of

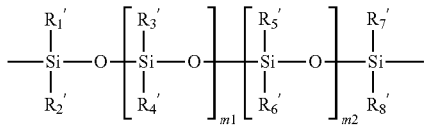

in which n1 and n2 independently of each other are an integer of from 0 to 500 and (m1+m2) is from 2 to 500, $R_1'$, $R_2'$, $R_3'$, $R_4'$, $R_5'$, $R_6'$, $R_7'$, and $R_8'$ independently of one another, are $C_1$-$C_{10}$ alkyl, $C_1$-$C_4$ alkyl- or $C_1$-$C_4$-alkoxy-substituted phenyl, $C_1$-$C_{10}$ fluoroalkyl, $C_1$-$C_{10}$ fluoroether, $C_6$-$C_{18}$ aryl radical, -alk-$(OC_2H_4)_{m3}$—OR° (in which alk is $C_1$-$C_6$-alkylene divalent radical, R° is H or $C_1$-$C_{10}$ alkyl and m3 is an integer from 1 to 10), or a linear hydrophilic polymer chain.

The term "fluid" as used herein indicates that a material is capable of flowing like a liquid.

The term "alkyl" refers to a monovalent radical obtained by removing a hydrogen atom from a linear or branched alkane compound. An alkyl group (radical) forms one bond with one other group in an organic compound.

The term "alkylene divalent group" or "alkyl diradical" interchangeably refers to a divalent radical obtained by removing one hydrogen atom from an alkyl. An alkylene divalent group (or radical) forms two bonds with other groups in an organic compound.

The term "alkoxy" or "alkoxyl" refers to a monovalent radical obtained by removing the hydrogen atom from the hydroxyl group of a linear or branched alkyl alcohol. An alkoxy group (radical) forms one bond with one other group in an organic compound.

In this application, the term "substituted" in reference to an alkylene diradical or an alkyl radical means that the alkylene diadical or the alkyl radical comprises at least one substituent which replaces one hydrogen atom of the alkylene diradical or alkyl radical and is selected from the group consisting of hydroxyl (—OH), carboxy (—COOH), —$NH_2$, sulfhydryl (—SH), $C_1$-$C_4$ alkyl, $C_1$-$C_4$ alkoxy, $C_1$-$C_4$ alkylthio (alkyl sulfide), $C_1$-$C_4$ acylamino, $C_1$-$C_4$ alkylamino, di-$C_1$-$C_4$ alkylamino, halogen atom (Br or Cl), and combinations thereof.

A free radical initiator can be either a photoinitiator or a thermal initiator. A "photoinitiator" refers to a chemical that initiates free radical crosslinking/polymerizing reaction by the use of light. A "thermal initiator" refers to a chemical that initiates radical crosslinking/polymerizing reaction by the use of heat energy.

A "UV-absorbing vinylic monomer" refers to a compound comprising an ethylenically-unsaturated group and a UV-absorbing moiety which can absorb or screen out UV radiation in the range from 200 nm to 400 nm as understood by a person skilled in the art.

A "spatial limitation of actinic radiation" refers to an act or process in which energy radiation in the form of rays is directed by, for example, a mask or screen or combinations thereof, to impinge, in a spatially restricted manner, onto an area having a well defined peripheral boundary. A spatial limitation of UV radiation is obtained by using a mask or screen having a radiation (e.g., UV) permeable region, a radiation (e.g., UV) impermeable region surrounding the radiation-permeable region, and a projection contour which is the boundary between the radiation-impermeable and radiation-permeable regions, as schematically illustrated in the drawings of U.S. Pat. No. 6,800,225 (FIGS. 1-11), and U.S. Pat. No. 6,627,124 (FIGS. 1-9), U.S. Pat. No. 7,384,590 (FIGS. 1-6), and U.S. Pat. No. 7,387,759 (FIGS. 1-6), all of which are incorporated by reference in their entireties. The mask or screen allows to spatially projects a beam of radiation (e.g., UV radiation) having a cross-sectional profile defined by the projection contour of the mask or screen. The projected beam of radiation (e.g., UV radiation) limits radiation (e.g., UV radiation) impinging on a lens formulation located in the path of the projected beam from the first molding surface to the second molding surface of a mold. The resultant contact lens comprises an anterior surface defined by the first molding surface, an opposite posterior surface defined by the second molding surface, and a lens edge defined by the sectional profile of the projected UV beam (i.e., a spatial limitation of radiation). The radiation used for the crosslinking is radiation energy, especially UV radiation, gamma radiation, electron radiation or thermal radiation, the radiation energy preferably being in the form of a substantially parallel beam in order on the one hand to achieve good restriction and on the other hand efficient use of the energy.

As used in this application, the term "ethylenically functionalized" in reference to a compound or polymer or copolymer having one or more reactive functional groups (e.g., amine, hydroxyl, carboxyl, isocyanate, anhydride, and/or epoxy groups) means a process or product thereof in which one or more ethylenically unsaturated groups are covalently attached to the functional groups of the compound or polymer or copolymer by reacting an ethylenically functionalizing vinylic monomer with the compound or polymer or copolymer under coupling reaction conditions.

An "ethylenically functionalizing vinylic monomer" throughout of this patent application refers to a vinylic monomer having one reactive functional group capable of participating in a coupling (or crosslinking) reaction known to a person skilled in the art. Examples of ethylenically-functionalizing vinylic monomers include without limitation $C_2$ to $C_6$ hydroxylalkyl (meth)acrylate, $C_2$ to $C_6$ hydroxyalkyl (meth)acrylamide, allylalcohol, allylamine, amino-$C_2$-$C_6$ alkyl (meth)acrylate, $C_1$-$C_6$ alkylamino-$C_2$-$C_6$ alkyl (meth)acrylate, vinylamine, amino-$C_2$-$C_6$ alkyl (meth)acrylamide, $C_1$-$C_3$ alkylamino-$C_2$-$C_6$ alkyl (meth)acrylamide, acrylic acid, $C_1$-$C_4$ alkylacrylic acid (e.g., methacrylic ethylacrylic acid, propylacrylic acid, butylacrylic acid), N-[tris(hydroxymethyl)-methyl]acrylamide, N,N-2-acrylamidoglycolic acid, beta methyl-acrylic acid (crotonic acid), alpha-phenyl acrylic acid, beta-acryloxy propionic acid, sorbic acid, angelic acid, cinnamic acid, 1-carboxy-4-phenyl butadiene-1,3, itaconic acid, citraconic acid, mesaconic acid, glutaconic acid, aconitic acid, maleic acid, fumaric acid, aziridinyl $C_1$-$C_{12}$ alkyl (meth)acrylate (e.g., 2-(1-aziridinyl) ethyl (meth)acrylate, 3-(1-aziridinyl) propyl (meth)acrylate, 4-(1-aziridinyl) butyl (meth)acrylate, 6-(1-aziridinyl) hexyl (meth)acrylate, or 8-(1-aziridinyl) octyl (meth)acrylate), glycidyl (meth)acrylate, vinyl glycidyl ether, allyl glycidyl ether, (meth)acryloyl halide groups ($CH_2$=CH—COX or $CH_2$=$CCH_3$—COX, X=Cl or Br), N-hydroxysuccinimide ester of (meth)acrylic acid, $C_1$ to $C_6$ isocyanatoalkyl (meth)acrylate, azlactone-containing vinylic monomers (e.g., 2-vinyl-4,4-dimethyl-1,3-oxazolin-5-one, 2-isopropenyl-4,4-dimethyl-1,3-oxazolin-5-one, 2-vinyl-4-methyl-4-ethyl-1,3-oxazolin-5-one, 2-isopropenyl-4-methyl-4-butyl-1,3-oxazolin-5-one, 2-vinyl-4,4-dibutyl-1,3-oxazolin-5-one, 2-isopropenyl-4-methyl-4-dodecyl-1,3-oxazolin-5-one, 2-isopropenyl-4,4-diphenyl-1,3-oxazolin-5-one, 2-isopropenyl-4,4-pentamethylene-1,3-oxazolin-5-one, 2-isopropenyl-4,4-tetramethylene-1,3-oxazolin-5-one, 2-vinyl-4,4-diethyl-1,3-oxazolin-5-one, 2-vinyl-4-methyl-4-nonyl-1,3-oxazolin-5-one, 2-isopropenyl-4-methyl-4-phenyl-1,3-oxazolin-5-one, 2-isopropenyl-4-methyl-4-benzyl-1,3-oxazolin-5-one, 2-vinyl-4,4-pentamethylene-1,3-oxazolin-5-one, and 2-vinyl-4,4-dimethyl-1,3-oxazolin-6-one, with 2-vinyl-4,4-dimethyl-1,3-oxazolin-5-one (VDMO) and 2-isopropenyl-4,4-dimethyl-1,3-oxazolin-5-one (IPDMO) as preferred azlactone-containing vinylic monomers), and combinations thereof.

The intrinsic "oxygen permeability", Dk, of a material is the rate at which oxygen will pass through a material. As used in this application, the term "oxygen permeability (Dk)" in reference to a hydrogel (silicone or non-silicone) or a contact lens means an oxygen permeability (Dk) which is measured at and corrected for the surface resistance to oxygen flux caused by the boundary layer effect according to the procedures shown in Examples hereinafter. Oxygen permeability is conventionally expressed in units of barrers, where "barrer" is defined as $[(cm^3\ oxygen)(mm)/(cm^2)(sec)(mm\ Hg)]\times 10^{-10}$.

The "oxygen transmissibility", Dk/t, of a lens or material is the rate at which oxygen will pass through a specific lens or material with an average thickness of t [in units of mm] over the area being measured. Oxygen transmissibility is conventionally expressed in units of barrers/mm, where "barrers/mm" is defined as $[(cm^3\ oxygen)/(cm^2)(sec)(mm\ Hg)]\times 10^{-9}$.

The term "modulus" or "elastic modulus" in reference to a contact lens or a material means the tensile modulus or Young's modulus which is a measure of the stiffness of a contact lens or a material. The modulus can be measured using a method in accordance with ANSI Z80.20 standard. A person skilled in the art knows well how to determine the elastic modulus of a silicone hydrogel material or a contact lens. For example, all commercial contact lenses have reported values of elastic modulus.

The term "thermal stability" in reference to a silicone hydrogel contact lens means that the silicone hydrogel contact lens can be stored for a period of time at an elevated temperature (e.g., 40° C., 50° C., 55° C., 60° C., 65° C., 70° C., 80° C., or 90° C.) without significant change in elastic modulus (i.e., an increase or decrease in elastic modulus of about 10% or less, preferably about 5% or less, relative to the elastic modulus of the silicone hydrogel contact lens before being stored at the elevated temperature).

In general, the invention is directed to carbosiloxane vinylic monomers and uses in preparing a polymer (preferably a silicone hydrogel material), and a medical device (preferably silicone hydrogel contact lenses). A carbosiloxane vinylic monomer of the invention comprises: one sole actinically polymerizable terminal group (which is preferably an ethylenically unsaturated group, more preferably (meth)acryloyl group); one sole terminal butyl group; and one oligo(carbosiloxane)-containing linkage between the actinically polymerizable terminal group and the terminal butyl group. Unlike a tris(trialkylsilyloxy)silylalkyl-containing vinylic monomer, a carbosiloxane vinylic monomer is hydrolytically resistant. But, like a tris(trialkylsilyloxy)silylalkyl-containing vinylic monomer, a carbosiloxane vinylic monomer can be served as a compatibilizing agent to compatibilize hydrophilic components with hydrophobic components (e.g., polysiloxane monomer(s) and/or polysiloxane macromere(s), or the likes) in a silicone hydrogel lens formulation so as to produce silicone hydrogel contact lenses with high optical quality. A carbosiloxane vinylic monomer of the invention can be used to substitute tris(trialkylsilyloxy)silylalkyl-containing vinylic monomer in a silicone hydrogel lens formulation for making silicone hydrogel contact lenses having a relatively high oxygen permeability, a relatively low elastic modulus, and a thermal stability (i.e., relatively high hydrolytic resistance).

The present invention, in one aspect, provides a carbosiloxane vinylic monomer being represented by formula (I)

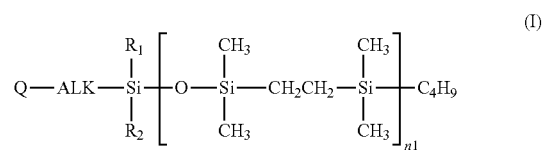

in which: n1 is an integer of 2 to 5; ALK is a $C_1$-$C_6$ alkyl diradical; $R_1$ and $R_2$ independent of each another are a $C_1$-$C_6$ alkyl radical; Q is an ethylenically unsaturated group selected from the group consisting of

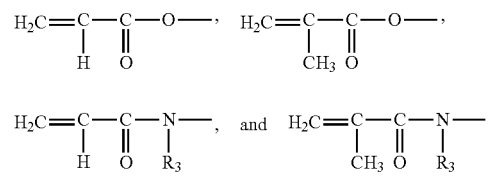

in which $R_3$ is hydrogen or a $C_1$-$C_6$ alkyl radical.

A carbosiloxane vinylic monomers of formula (I) can be prepared from 2,2,5,5-tetramethyl-2,5-disila-1-oxacyclopentane according to various schemes. For example, a carbosiloxane vinylic monomer of formula I can be prepared by initiating the "living" polymerization of 2,2,5,5-tetramethyl-2,5-disila-1-oxacyclopentane with n-butyllithium (or sec-butyllithium or iso-butyllithium, or t-butyllithium) and quenching the reaction with methacryloxypropyl dimethylchlorosilane, as illustrated in Scheme I.

Scheme I

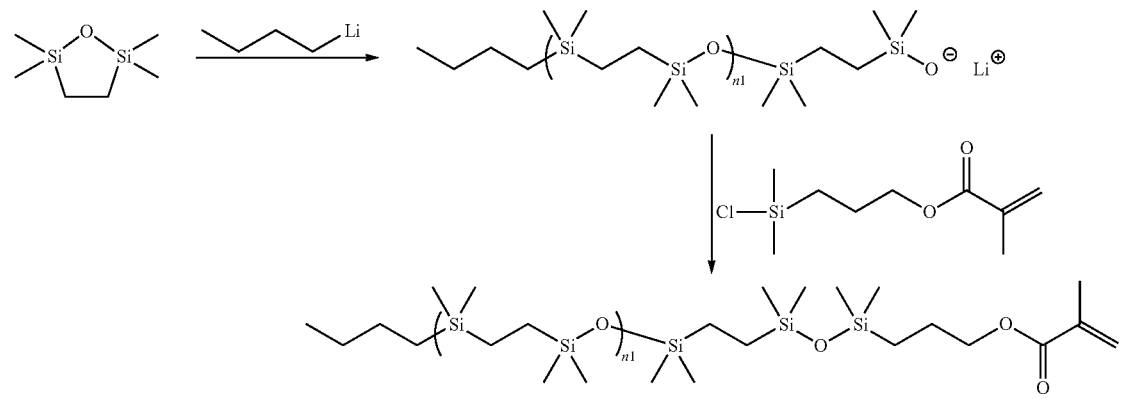

nl = 1-4

A carbosiloxane vinylic monomer of formula (I) can also be prepared by initiating the "living" polymerization of 2,2,5,5-tetramethyl-2,5-disila-1-oxacyclopentane with n-butyllithium (or sec-butyllithium or iso-butyllithium, or t-butyllithium), quenching the reaction with dialkylchlorosilane (e.g., dimethylchlorosilane, diethylchlorosilane, etc.), followed by hydrosilylation with allymethacrylamide or allymethacrylate, as illustrated in Scheme II.

cone-containing actinically-crosslinkable prepolymer or a silicone hydrogel polymeric material, which is another aspect of the invention.

In another aspect, the invention is related to a polymer comprising monomeric units derived in a free-radical polymerization from a carbosiloxane vinylic monomer of formula (I) as defined above.

Scheme II

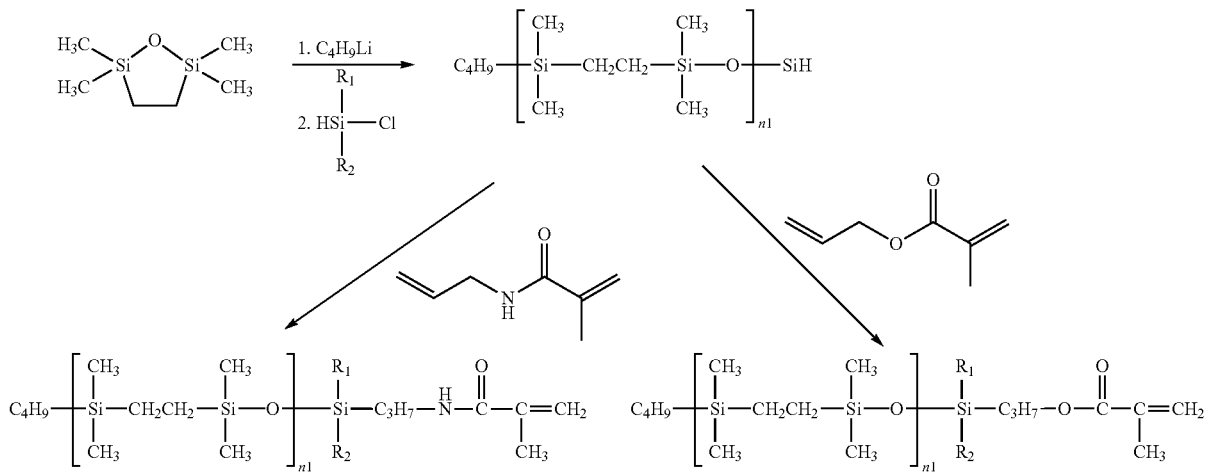

A carbosiloxane vinylic monomer of formula (I) can also be prepared by initiating the "living" polymerization of 2,2,5,5-tetramethyl-2,5-disila-1-oxacyclopentane with n-butyllithium (or sec-butyllithium or iso-butyllithium, or t-butyllithium), quenching the reaction with dialkylchlorosilane (e.g., dimethylchlorosilane, diethylchlorosilane, etc.), followed by hydrosilylation with an ene-containing monomer having an amino or hydroxyl group (e.g., allylamine, 3-butenylamine, 4-pentenylamine, 5-hexenylamine, allyl alcohol, allylcarbinol, allyethyl alcohol, 5-hexen-1-ol, 5-hexen-2-ol) to obtained carbosiloxane compound terminated with one butyl group and one amino or hydroxyl group, and then reacting the amino or hydroxyl group of the carbosiloxane compound with acrylic acid chloride or methacrylic acid chloride.

A carbosiloxane vinylic monomer of formula (I) as defined above can find use in preparing a polymer, preferably a sili- In this aspect of the invention, a polymer can be a copolymer soluble or insoluble in a solvent, preferably an actinically-crosslinkable prepolymer or a silicone hydrogel material.

A person skilled in the art knows how to prepare a polymer, an actinically-crosslinkable silicone-containing prepolymer, or a silicone hydrogel material from a polymerizable composition according to any known free-radical polymerization mechanism. The polymerizable composition for preparing a polymer, an actinically-crosslinkable silicone containing prepolymer (i.e., an intermediary copolymer for the prepolymer), or a silicone hydrogel polymeric material of the invention can be a melt, a solventless liquid in which all necessary components are blended together, or a solution in which all necessary component is dissolved in an inert solvent, such as water, an organic solvent, or mixture thereof, as known to a person skilled in the art.

Example of suitable solvents includes without limitation, water, tetrahydrofuran, tripropylene glycol methyl ether, dipropylene glycol methyl ether, ethylene glycol n-butyl ether, ketones (e.g., acetone, methyl ethyl ketone, etc.), diethylene glycol n-butyl ether, diethylene glycol methyl ether, ethylene glycol phenyl ether, propylene glycol methyl ether, propylene glycol methyl ether acetate, dipropylene glycol methyl ether acetate, propylene glycol n-propyl ether, dipropylene glycol n-propyl ether, tripropylene glycol n-butyl ether, propylene glycol n-butyl ether, dipropylene glycol n-butyl ether, tripropylene glycol n-butyl ether, propylene glycol phenyl ether dipropylene glycol dimetyl ether, polyethylene glycols, polypropylene glycols, ethyl acetate, butyl acetate, amyl acetate, methyl lactate, ethyl lactate, i-propyl lactate, methylene chloride, 2-butanol, 1-propanol, 2-propanol, menthol, cyclohexanol, cyclopentanol and exonorborneol, 2-pentanol, 3-pentanol, 2-hexanol, 3-hexanol, 3-methyl-2-butanol, 2-heptanol, 2-octanol, 2-nonanol, 2-decanol, 3-octanol, norborneol, tert-butanol, tert-amyl, alcohol, 2-methyl-2-pentanol, 2,3-dimethyl-2-butanol, 3-methyl-3-pentanol, 1-methylcyclohexanol, 2-methyl-2-hexanol, 3,7-dimethyl-3-octanol, 1-chloro-2-methyl-2-propanol, 2-methyl-2-heptanol, 2-methyl-2-octanol, 2-2-methyl-2-nonanol, 2-methyl-2-decanol, 3-methyl-3-hexanol, 3-methyl-3-heptanol, 4-methyl-4-heptanol, 3-methyl-3-octanol, 4-methyl-4-octanol, 3-methyl-3-nonanol, 4-methyl-4-nonanol, 3-methyl-3-octanol, 3-ethyl-3-hexanol, 3-methyl-3-heptanol, 4-ethyl-4-heptanol, 4-propyl-4-heptanol, 4-isopropyl-4-heptanol, 2,4-dimethyl-2-pentanol, 1-methylcyclopentanol, 1-ethylcyclopentanol, 1-ethylcyclopentanol, 3-hydroxy-3-methyl-1-butene, 4-hydroxy-4-methyl-1-cyclopentanol, 2-phenyl-2-propanol, 2-methoxy-2-methyl-2-propanol 2,3, 4-trimethyl-3-pentanol, 3,7-dimethyl-3-octanol, 2-phenyl-2-butanol, 2-methyl-1-phenyl-2-propanol and 3-ethyl-3-pentanol, 1-ethoxy-2-propanol, 1-methyl-2-propanol, t-amyl alcohol, isopropanol, 1-methyl-2-pyrrolidone, N,N-dimethylpropionamide, dimethyl formamide, dimethyl acetamide, dimethyl propionamide, N-methyl pyrrolidinone, and mixtures thereof.

The copolymerization of a polymerizable composition for preparing a polymer, an actinically-crosslinkable silicone containing prepolymer (i.e., an intermediary copolymer for the prepolymer), or a silicone hydrogel polymeric material of the invention may be induced photochemically or thermally.

Suitable photoinitiators are benzoin methyl ether, diethoxyacetophenone, a benzoylphosphine oxide, 1-hydroxycyclohexyl phenyl ketone and Darocur and Irgacure types, preferably Darocur 1173®, Irgacure 369®, Irgacure 379®, and Irgacure 2959®. Examples of benzoylphosphine oxide initiators include 2,4,6-trimethylbenzoyldiphenylophosphine oxide (TPO); bis-(2,6-dichlorobenzoyl)-4-N-propylphenylphosphine oxide; and bis-(2,6-dichlorobenzoyl)-4-N-butylphenylphosphine oxide. Reactive photoinitiators which can be incorporated, for example, into a macromer or can be used as a special monomer are also suitable. Examples of reactive photoinitiators are those disclosed in EP 632 329, herein incorporated by reference in its entirety. The polymerization can then be triggered off by actinic radiation, for example light, in particular UV light of a suitable wavelength. The spectral requirements can be controlled accordingly, if appropriate, by addition of suitable photosensitizers.

Suitable thermal polymerization initiators are known to the skilled artisan and comprise, for example peroxides, hydroperoxides, azo-bis(alkyl- or cycloalkylnitriles), persulfates, percarbonates or mixtures thereof. Examples are benzoylperoxide, tert.-butyl peroxide, di-tert.-butyl-diperoxyphthalate, tert.-butyl hydroperoxide, azo-bis(isobutyronitrile) (AIBN), 1,1-azodiisobutyramidine, 1,1'-azo-bis(1-cyclohexanecarbonitrile), 2,2'-azo-bis(2,4-dimethyl-valeronitrile) and the like. The polymerization is carried out conveniently in an above-mentioned solvent at elevated temperature, for example at a temperature of from 25 to 100° C. and preferably 40 to 80° C. The reaction time may vary within wide limits, but is conveniently, for example, from 1 to 24 hours or preferably from 2 to 12 hours. It is advantageous to previously degas the components and solvents used in the polymerization reaction and to carry out said copolymerization reaction under an inert atmosphere, for example under a nitrogen or argon atmosphere.

Generally, a polymer of the invention is obtained by polymerizing thermally or actinically a polymerizable composition including a carbosiloxane vinylic monomer of formula (I) as defined above and one or more polymerizable components selected from the group consisting of a hydrophilic vinylic monomer, a hydrophobic vinylic monomer, a polysiloxane-containing vinylic monomer, a polysiloxane-containing crosslinker, a non-silicone crosslinker, a hydrophilic prepolymer, a UV-absorbing vinylic monomer, and combinations thereof. Various embodiments of all of the above-described polymerizable components are discussed below.

In accordance with the invention, any suitable hydrophilic vinylic monomers can be used in a polymerizable composition for preparing a polymer of the invention. Examples of preferred hydrophilic vinylic monomers include without limitation N-vinylpyrrolidone, N,N-dimethyl (meth)acrylamide, (meth)acrylamide, hydroxylethyl (meth)acrylamide, hydroxyethyl (meth)acrylate, glycerol methacrylate (GMA), polyethylene glycol (meth)acrylate, polyethylene glycol $C_1$-$C_4$-alkyl ether (meth)acrylate having a weight average molecular weight of up to 1500, N-vinyl formamide, N-vinyl acetamide, N-vinyl isopropylamide, N-vinyl-N-methyl acetamide, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, (meth)acrylic acid, ethylacrylic acid, and combinations thereof.

Any suitable hydrophobic vinylic monomers can be used in a polymerizable composition for making a polymer of the invention. By incorporating a certain amount of hydrophobic vinylic monomer in a monomer mixture, the mechanical properties (e.g., modulus of elasticity) of the resultant polymer may be improved. Examples of preferred hydrophobic vinylic monomers include methylacrylate, ethyl-acrylate, propylacrylate, isopropylacrylate, cyclohexylacrylate, 2-ethylhexylacrylate, methylmethacrylate, ethyl methacrylate, propylmethacrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyl toluene, vinyl ethyl ether, perfluorohexylethyl-thio-carbonyl-aminoethyl-methacrylate, isobornyl methacrylate, trifluoroethyl methacrylate, hexafluoro-isopropyl methacrylate, hexafluorobutyl methacrylate.

Any suitable polysiloxane-containing vinylic monomer (each comprising at least one polysiloxane segment and one sole ethylenically unsaturated group) can be used in a polymerizable composition for preparing a polymer of the invention. Preferred examples of such vinylic monomers are mono-(meth)acrylated polydimethylsiloxanes of various molecular weight (e.g., mono-3-methacryloxypropyl terminated, mono-$C_1$-$C_4$ alkyl terminated polydimethylsiloxane, or mono-(3-methacryloxy-2-hydroxypropyloxy)propyl terminated, mono-$C_1$-$C_4$ alkyl terminated polydimethylsiloxane). Alternatively, monoethylenically functionalized polysiloxanes can be obtained by ethylenically functionalizing of a monofunctionalized polysiloxanes (i.e., with one sole terminal functional group, such as, e.g., —$NH_2$, —OH, —COOH, epoxy group, halide, etc.) as described above. Suitable monofunctionalized polysiloxanes are commercially available, e.g., from Aldrich, ABCR GmbH & Co., Fluorochem, or Gelest, Inc, Morrisville, Pa.

Any suitable polysiloxane-containing crosslinkers (each of which comprises at least one polysiloxane segment and at least two ethylenically unsaturated groups) can be used in a polymerizable composition for preparing a polymer of the invention. Examples of polysiloxane-containing crosslinkers include without limitation, bis-(meth)acrylated polydimethylsiloxanes; bis-vinyl carbonate-terminated polydimethylsiloxanes; bis-vinyl carbamate-terminated polydimethylsiloxane; bis-vinyl terminated polydimethylsiloxanes; bis-(meth)acrylamide-terminated polydimethylsiloxanes; bis-3-methacryloxy-2-hydroxypropyloxypropyl polydimethylsiloxane; N,N,N',N'-tetrakis(3-methacryloxy-2-hydroxypropyl)-alpha,omega-bis-3-aminopropyl-polydimethylsiloxane; polysiloxane or chain-extended polysiloxane crosslinkers selected from the group consisting of Macromer A, Macromer B, Macromer C, and Macromer D described in U.S. Pat. No. 5,760,100 (herein incorporated by reference in its entirety); the reaction products of glycidyl (meth)acrylate with bis-aminoalkyl-terminated or bis-hydroxyalkoxyalkyl terminated polydimethylsiloxanes; the reaction products of hydroxy-containing or amino-containing vinylic monomer with bis-epoxyalkoxyalkyl-terminated polydimethylsiloxanes; polysiloxane-containing crosslinkers disclosed in U.S. Pat. Nos. 4,136,250, 4,153,641, 4,182,822, 4,189,546, 4,259,467, 4,260,725, 4,261,875, 4,343,927, 4,254,248, 4,355,147, 4,276,402, 4,327,203, 4,341,889, 4,486,577, 4,543,398, 4,605,712, 4,661,575, 4,684,538, 4,703,097, 4,833,218, 4,837,289, 4,954,586, 4,954,587, 5,010,141, 5,034,461, 5,070,170, 5,079,319, 5,039,761, 5,346,946, 5,358,995, 5,387,632, 5,416,132, 5,451,617, 5,486,579, 5,962,548, 5,981,675, 6,039,913, 6,762,264, 7,091,283, 7,238,750, 7,268,189, 7,566,754, 7,956,135, 8,071,696, 8,071,703, 8,071,658, 8,048,968, 8,283, 429, 8,263,679, 8,044,111, and 8,211,955 and in published US patent application Nos. 2008/0015315 A1, 2010/0120939 A1, 2010/0298446 A1, 2010/0296049 A1, 2011/0063567 A1, 2012/0088843 A1, 2012/0088844 A1, 2012/0029111 A1, and 2012/0088861 A1 (herein incorporated by reference in their entireties).

Any suitable non-silicone crosslinkers can be used in a polymerizable composition for preparing a polymer of the invention. Examples of preferred non-silicone crosslinkers include without limitation tetraethyleneglycol di-(meth)acrylate, triethyleneglycol di-(meth)acrylate, ethyleneglycol di-(meth)acrylate, diethyleneglycol di-(meth)acrylate, bisphenol A dimethacrylate, vinyl methacrylate, ethylenediamine di(meth)acrylamide, glycerol dimethacrylate, allyl(meth)acrylate, N,N'-methylenebis(meth)acrylamide, N,N'-ethylenebis(meth)acrylamide, N,N'-dihydroxyethylene bis(meth)acrylamide, a product of diamine (preferably selected from the group consisting of N,N'-bis(hydroxyethyl)ethylenediamine, N,N'-dimethylethylenediamine, ethylenediamine, N,N'-dimethyl-1,3-propanediamine, N,N'-diethyl-1,3-propanediamine, propane-1,3-diamine, butane-1,4-diamine, pentane-1,5-diamine, hexamethylenediamine, isophorone diamine, and combinations thereof) and epoxy-containing vinylic monomer (preferably selected from the group consisting of glycidyl (meth)acrylate, vinyl glycidyl ether, allyl glycidyl ether, and combinations thereof), combinations thereof. A more preferred crosslinker to be used in the preparation of a polymer, an actinically-crosslinkable silicone containing prepolymer, or a silicone hydrogel polymeric material of the invention is a hydrophilic crosslinker selected from the group consisting of tetra(ethyleneglycol) diacrylate, tri(ethyleneglycol) diacrylate, ethyleneglycol diacrylate, di(ethyleneglycol) diacrylate, glycerol dimethacrylate, allyl(meth)acrylate, N,N'-methylene bis(meth)acrylamide, N,N'-ethylene bis(meth)acrylamide, N,N'-dihydroxyethylene bis(meth)acrylamide, and combinations thereof.

Examples of hydrophilic prepolymers with multiple acryloyl or methacryloyl groups include, but are not limited to, a water-soluble crosslinkable poly(vinyl alcohol) prepolymer described in U.S. Pat. Nos. 5,583,163 and 6,303,687; a water-soluble vinyl group-terminated polyurethane prepolymer described in U.S. Patent Application Publication No. 2004/0082680; derivatives of a polyvinyl alcohol, polyethyleneimine or polyvinylamine, which are disclosed in U.S. Pat. No. 5,849,841; a water-soluble crosslinkable polyurea prepolymer described in U.S. Pat. No. 6,479,587 and in U.S. Published Application No. 2005/0113549; crosslinkable polyacrylamide; crosslinkable statistical copolymers of vinyl lactam, MMA and a comonomer, which are disclosed in EP 655,470 and U.S. Pat. No. 5,712,356; crosslinkable copolymers of vinyl lactam, vinyl acetate and vinyl alcohol, which are disclosed in EP 712,867 and U.S. Pat. No. 5,665,840; polyether-polyester copolymers with crosslinkable side chains which are disclosed in EP 932,635 and U.S. Pat. No. 6,492,478; branched polyalkylene glycol-urethane prepolymers disclosed in EP 958,315 and U.S. Pat. No. 6,165,408; polyalkylene glycol-tetra(meth)acrylate prepolymers disclosed in EP 961,941 and U.S. Pat. No. 6,221,303; and crosslinkable polyallylamine gluconolactone prepolymers disclosed in International Application No. WO 2000/31150 and U.S. Pat. No. 6,472,489.

Any suitable UV-absorbing vinylic monomers can be used in a polymerizable composition for preparing a polymer of the invention. Examples of preferred UV-absorbing and UV/HEVL-absorbing, benzotriazole-containing vinylic monomers include without limitation: 2-(2-hydroxy-5-vinylphenyl)-2H-benzotriazole, 2-(2-hydroxy-5-acrylyloxyphenyl)-2H-benzotriazole, 2-(2-hydroxy-3-methacrylamido methyl-5-tert octylphenyl)benzotriazole, 2-(2'-hydroxy-5'-methacrylamidophenyl)-5-chlorobenzotriazole, 2-(2'-hydroxy-5'-methacrylamidophenyl)-5-methoxybenzotriazole, 2-(2'-hydroxy-5'-methacryloxypropyl-3'-t-butylphenyl)-5-chlorobenzotriazole, 2-(2'-hydroxy-5'-methacryloxypropylphenyl)benzotriazole, 2-hydroxy-5-methoxy-3-(5-(trifluoromethyl)-2H-benzo[d][1,2,3]triazol-2-yl)benzyl methacrylate (WL-1), 2-hydroxy-5-methoxy-3-(5-methoxy-2H-benzo[d][1,2,3]triazol-2-yl)benzyl methacrylate (WL-5), 3-(5-fluoro-2H-benzo[d][1,2,3]triazol-2-yl)-2-hydroxy-5-methoxybenzyl methacrylate (WL-2), 3-(2H-benzo[d][1,2,3]triazol-2-yl)-2-hydroxy-5-methoxybenzyl methacrylate (WL-3), 3-(5-chloro-2H-benzo[d][1,2,3]triazol-2-yl)-2-hydroxy-5-methoxybenzyl methacrylate (WL-4), 2-hydroxy-5-methoxy-3-(5-methyl-2H-benzo[d][1,2,3]triazol-2-yl)benzyl methacrylate (WL-6), 2-hydroxy-5-methyl-3-(5-(trifluoromethyl)-2H-benzo[d][1,2,3]triazol-2-yl)benzyl methacrylate (WL-7), 4-allyl-2-(5-chloro-2H-benzo[d][1,2,3]triazol-2-yl)-6-methoxyphenol (WL-8), 2-{2'-Hydroxy-3'-tert-5'[3"-(4"-vinylbenzyloxy)propoxy]phenyl}-5-methoxy-2H-benzotriazole, phenol, 2-(5-chloro-2H-benzotriazol-2-yl)-6-(1,1-dimethylethyl)-4-ethenyl- (UVAM), 2-(2'-hydroxy-5'-methacryloxyethylphenyl) benzotriazole (2-Propenoic acid, 2-methyl-, 2-[3-(2H-benzotriazol-2-yl)-4-hydroxyphenyl]ethyl ester, Norbloc), 2-{2'-Hydroxy-3'-tert-butyl-5'-[3'-methacryloyloxypropoxy]phenyl}-5-methoxy-2H-benzotriazole (UV13), 2-[2'-Hydroxy-3'-tert-butyl-5'-(3'-acryloyloxypropoxyl)phenyl]-5-trifluoromethyl-2H-benzotriazole (CF$_3$-UV13), 2-(2'-hydroxy-5-methacrylamidophenyl)-5-methoxybenzotriazole (UV6), 2-(3-allyl-2-hydroxy-5-methylphenyl)-2H-benzotriazole (UV9), 2-(2-Hydroxy-3-methallyl-5-methylphenyl)-2H-benzotriazole (UV12), 2-3'-t-butyl-2'-hydroxy-5'-(3"-dimethylvinylsilylpropoxy)-2'-hydroxy-phenyl)-5-methoxybenzotriazole (UV15), 2-(2'- hydroxy-5'-methacryloylpropyl-3'-tert-butyl-phenyl)-5-methoxy-2H-benzotriazole (UV16), 2-(2'-hydroxy-5'-acryloylpropyl-3'-tert-butyl-phenyl)-5-methoxy-2H-benzotriazole (UV16A), 2-Methylacrylic acid 3-[3-tert-butyl-5-(5-chlorobenzotriazol-2-yl)-4-hydroxyphenyl]-propyl ester (16-100, CAS#96478-15-8), 2-(3-(tert-butyl)-4-hydroxy-5-(5-methoxy-2H-benzo[d][1,2,3]triazol-2-yl)phenoxy)ethyl methacrylate (16-102); Phenol, 2-(5-chloro-2H-benzotriazol-2-yl)-6-methoxy-4-(2-propen-1-yl) (CAS#1260141-20-5); 2-[2-Hydroxy-5-[3-(methacryloyloxy)propyl]-3-tert-butylphenyl]-5-chloro-2H-benzotriazole; Phenol, 2-(5-ethenyl-2H-benzotriazol-2-yl)-4-methyl-, homopolymer (9Cl) (CAS#83063-87-0). In accordance with the invention, the polymerizable composition comprises about 0.2% to about 5.0%, preferably about 0.3% to about 2.5%, more preferably about 0.5% to about 1.8%, by weight of a UV-absorbing agent.

Where a vinylic monomer capable of absorbing ultra-violet radiation and high energy violet light (HEVL) is used in the invention, a Germane-based Norrish Type I photoinitiator and a light source including a light in the region of about 400 to about 550 nm are preferably used to initiate a free-radical polymerization. Any Germane-based Norrish Type I photoinitiators can be used in this invention, so long as they are capable of initiating a free-radical polymerization under irradiation with a light source including a light in the region of about 400 to about 550 nm. Examples of Germane-based Norrish Type I photoinitiators are acylgermanium compounds described in U.S. Pat. No. 7,605,190 (herein incorporated by reference in its entirety). Preferably, the monomer of lens-forming materials comprises at least one of the following acylgermanium compounds.

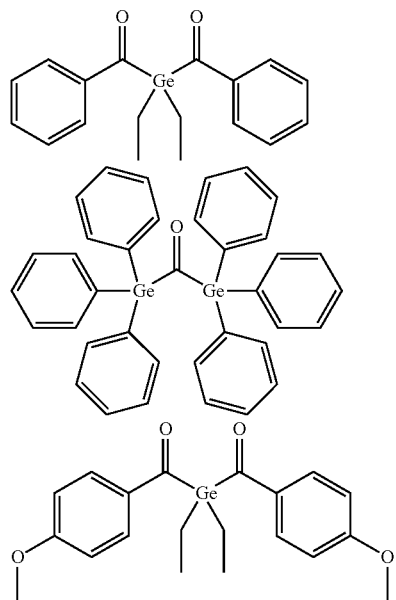

In a preferred embodiment, a polymer of the invention is a silicone-containing actinically-crosslinkable prepolymer, which preferably comprises: (1) monomeric units derived from a carbosiloxane vinylic monomer of formula (I) as defined above; (2) crosslinking units derived from at least one polysiloxane-containing crosslinker as described above and/or polysiloxane units derived from a polysiloxane-containing vinylic monomer as described above, (3) hydrophilic units derived from at least one hydrophilic vinylic monomer as described above; (4) polymerizable units derived from a chain transfer agent having a first reactive functional group other than thiol group and/or a vinylic monomer having a second reactive functional group other than ethylenically-unsaturated group, wherein the polymerizable units each comprise an ethylenically unsaturated group covalently attached to one polymerizable unit through the first or second reactive functional group; (5) optionally non-silicone crosslinking units derived from at least one non-silicone crosslinker as described above; and (6) optionally UV-absorbing units derived from a UV-absorbing vinylic monomer as described above. Such a prepolymer is capable of being actinically crosslinked, in the absence of one or more vinylic monomers, to form a silicone hydrogel contact lens having a water content of from about 20% to about 75% (preferably from about 25% to about 70%, more preferably from about 30% to about 65%) by weight when fully hydrated, and an oxygen permeability (Dk) of at least about 40 barrers (preferably at least about 50 barrers, more preferably at least about 60 barrers, and even more preferably at least about 70 barrers). Preferably, such a prepolymer is water soluble or processable and has a high water solubility or dispersibility of at least about 5%, preferably at least about 10%, more preferably at least about 20% by weight in water. An actinically-crosslinkable silicone-containing prepolymer of the invention can find particular use in preparing silicone hydrogel ophthalmic lenses, in particular contact lenses.

Such a prepolymer is obtained by first polymerizing a polymerizable composition including all polymerizable components specified above, to form an intermediary copolymer and then by ethylenically functionalizing the intermediary copolymer with an ethylenically functionalizing vinylic monomer having a third reactive functional group capable of reacting with the first and/or second reactive functional group to form a linkage in a coupling reaction in the presence or absence of a coupling agent to form the prepolymer, wherein the first, second and third reactive functional groups independent of one another are selected from the group consisting of amino group, hydroxyl group, carboxyl group, acid halide group, azlactone group, isocyanate group, epoxy group, aziridine group, and combination thereof. The general procedures for preparing amphiphilic prepolymers are disclosed in U.S. Pat. Nos. 6,039,913, 6,043,328, 7,091,283, 7,268,189 and 7,238,750, 7,521,519, 8,071,703, 8,044,111, and 8,048,968; in US patent application publication Nos. US 2008-0015315 A1, US 2008-0143958 A1, US 2008-0143003 A1, US 2008-0234457 A1, US 2008-0231798 A1, 2010/0120939 A1, 2010/0298446 A1, 2012/0088843 A1, 2012/0088844 A1, and 2012/0088861 A1; all of which are incorporated herein by references in their entireties.

In accordance with the invention, the polymerizable units each comprise a basic monomeric unit being a part of a polymer chain of the prepolymer and a pendant or terminal, ethylenically-unsaturated group attached thereon, wherein each basic monomeric unit is derived from a first ethylenically functionalizing vinylic monomer having a second reactive functional group, wherein the pendant or terminal ethylenically unsaturated group is derived from a second ethylenically functionalizing vinylic monomer having a third reactive functional group which reacts with one second reactive functional in the presence or absence of a crosslinking agent to form a covalent linkage. The second and third reactive functional groups are selected from the group consisting of amino group, hydroxyl group, carboxyl group, azlactone group, isocyanate group, epoxy group, aziridine group, acid chloride, and combination thereof. Examples of such vinylic monomers are those ethylenically functionalizing vinylic monomers described above. Preferably, the first ethylenically functionalizing vinylic monomer is any one of those described above.

In accordance with the invention, the content of the polymerizable units are determined based on weight percentage of the ethylenically functionalizing vinylic monomer present in the polymerizable composition for making an intermediary copolymer relative to the total weight of polymerizable components in the polymerizable composition or the weight percentage of the ethylenically functionalizing vinylic monomer used in ethylenically functionalizing the intermediary copolymer to form the prepolymer of the invention, relative to the weight of the prepolymer.

A chain transfer agent (containing at least one thiol group) is used to control the molecular weight of the resultant intermediary copolymer. Where a chain transfer has a reactive functional group such as amine, hydroxyl, carboxyl, epoxy, isocyanate, azlactone, or aziridine group, it can provide terminal or pendant functionality (amine, hydroxyl, carboxyl, epoxy, isocyanate, azlactone, or aziridine group) for subsequent ethylenical functionalization of the resultant intermediary copolymer.

In another preferred embodiment, a polymer of the invention is a silicone hydrogel material which is obtained by thermally or actinically polymerizing a polymerizable composition which preferably comprises a carbosiloxane vinylic monomer of formula (I) as defined above and/or an actinically-crosslinkable prepolymer of the invention as described above. A silicone hydrogel material of the invention preferably is the bulk material of a soft contact lens which is obtained by polymerizing the polymerizable composition in a mold, wherein the contact lens has a water content of from about 20% to about 75% (preferably from about 25% to about 70%, more preferably from about 30% to about 65%) by weight when fully hydrated, an oxygen permeability (Dk) of at least about 40 barrers (preferably at least about 50 barrers, more preferably at least about 60 barrers, and even more preferably at least about 70 barrers), and an elastic modulus of from about 0.1 MPa to about 2.0 MPa, preferably from about 0.2 MPa to about 1.5 MPa, more preferably from about 0.3 MPa to about 1.2 MPa, even more preferably from about 0.4 MPa to about 1.0 MPa. The polymerizable composition for obtaining a soft contact lens of the invention can further comprise one or more components selected from the group consisting of a hydrophilic vinylic monomer (any one of those described above), a hydrophobic vinylic monomer (any one of those described above), a polysiloxane-containing vinylic monomer (any one of those described above), a polysiloxane-containing crosslinker (any one of those described above), a non-silicone crosslinker (any one of those described above), a photoinitiator (any one of those described above), a thermal initiator (any one of those described above), a UV-absorbing vinylic monomer (any one of those described above), a visibility tinting agent (e.g., dyes, pigments, or mixtures thereof), antimicrobial agents (e.g., preferably silver nanoparticles), a bioactive agent (e.g., rebamipide, ketotifen, olaptidine, cromoglycolate, cyclosporine, nedocromil, levocabastine, lodoxamide, ketotifen, or the pharmaceutically acceptable salt or ester thereof, 2-pyrrolidone-5-carboxylic acid, vitamins, or mixtures thereof), leachable lubricants (e.g., polyglycolic acid, a water-soluble non-crosslinkable hydrophilic polymer), leachable tear-stabilizing agents (e.g., phospholipids), and mixtures thereof.

A person skilled in the art knows well how to measure the oxygen permeability, oxygen transmissibility, water content and elastic modulus of silicone hydrogel contact lenses. These lens properties have been reported by all manufacturers for their silicone hydrogel contact lens products.

Lens molds for making contact lenses are well known to a person skilled in the art and, for example, are employed in cast molding or spin casting. For example, a mold (for cast molding) generally comprises at least two mold sections (or portions) or mold halves, i.e. first and second mold halves. The first mold half defines a first molding (or optical) surface and the second mold half defines a second molding (or optical) surface. The first and second mold halves are configured to receive each other such that a lens forming cavity is formed between the first molding surface and the second molding surface. The molding surface of a mold half is the cavity-forming surface of the mold and in direct contact with lens-forming material.

Methods of manufacturing mold sections for cast-molding a contact lens are generally well known to those of ordinary skill in the art. The process of the present invention is not limited to any particular method of forming a mold. In fact, any method of forming a mold can be used in the present invention. The first and second mold halves can be formed through various techniques, such as injection molding or lathing. Examples of suitable processes for forming the mold halves are disclosed in U.S. Pat. No. 4,444,711 to Schad; U.S. Pat. No. 4,460,534 to Boehm et al.; U.S. Pat. No. 5,843,346 to Morrill; and U.S. Pat. No. 5,894,002 to Boneberger et al., which are also incorporated herein by reference.

Virtually all materials known in the art for making molds can be used to make molds for making contact lenses. For example, polymeric materials, such as polyethylene, polypropylene, polystyrene, PMMA, Topas® COC grade 8007-S10 (clear amorphous copolymer of ethylene and norbornene, from Ticona GmbH of Frankfurt, Germany and Summit, N.J.), or the like can be used. Other materials that allow UV light transmission could be used, such as quartz glass and sapphire.

In accordance with the invention, the polymerizable composition can be introduced (dispensed) into a cavity formed by a mold according to any known methods.

After the polymerizable composition is dispensed into the mold, it is polymerized to produce a contact lens. Crosslinking may be initiated thermally or actinically, preferably by exposing the lens-forming composition in the mold to a spatial limitation of actinic radiation to crosslink the polymerizable components in the polymerizable composition.

Opening of the mold so that the molded article can be removed from the mold may take place in a manner known per se.

The molded contact lens can be subject to lens extraction to remove unpolymerized polymerizable components. The extraction solvent can be any solvent known to a person skilled in the art. Examples of suitable extraction solvent are those described above. Preferably, water or an aqueous solution is used as extraction solvent. After extraction, lenses can be hydrated in water or an aqueous solution of a wetting agent (e.g., a hydrophilic polymer).

The molded contact lenses can further subject to further processes, such as, for example, surface treatment, packaging in lens packages with a packaging solution which can contain about 0.005% to about 5% by weight of a wetting agent (e.g., a hydrophilic polymer described above or the like known to a person skilled in the art) and/or a viscosity-enhancing agent (e.g., methyl cellulose (MC), ethyl cellulose, hydroxymethylcellulose, hydroxyethyl cellulose (HEC), hydroxypropylcellulose (HPC), hydroxypropylmethyl cellulose (HPMC), or a mixture thereof); sterilization such as autoclave at from 118 to 124° C. for at least about 30 minutes; and the like.

It is understood that a soft contact lens of the invention can optionally comprise minor amount of additional repeating units (i.e., less than about 5% by weight of total polymerizable components in a lens formulation for making the soft contact lens) derived from a hydrophilic vinylic monomer other than (meth)acrylamide-type vinylic monomer and/or a non-silicone hydrophobic vinylic monomer.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part or can be combined in any manner and/or used together. Therefore, the spirit and scope of the appended claims should not be limited to the description of the preferred versions contained therein.

The previous disclosure will enable one having ordinary skill in the art to practice the invention. In order to better enable the reader to understand specific embodiments and the advantages thereof, reference to the following non-limiting examples is suggested. However, the following examples should not be read to limit the scope of the invention.

Example 1

The apparent oxygen permeability of a lens and oxygen transmissibility of a lens material is determined according to a technique similar to the one described in U.S. Pat. No. 5,760,100 and in an article by Winterton et al., (The Cornea: Transactions of the World Congress on the Cornea 111, H. D. Cavanagh Ed., Raven Press: New York 1988, pp 273-280), both of which are herein incorporated by reference in their entireties. Oxygen fluxes (J) are measured at 34° C. in a wet cell (i.e., gas streams are maintained at about 100% relative humidity) using a Dk1000 instrument (available from Applied Design and Development Co., Norcross, Ga.), or similar analytical instrument. An air stream, having a known percentage of oxygen (e.g., 21%), is passed across one side of the lens at a rate of about 10 to 20 cm$^3$/min., while a nitrogen stream is passed on the opposite side of the lens at a rate of about 10 to 20 cm$^3$/min. A sample is equilibrated in a test media (i.e., saline or distilled water) at the prescribed test temperature for at least 30 minutes prior to measurement but not more than 45 minutes. Any test media used as the overlayer is equilibrated at the prescribed test temperature for at least 30 minutes prior to measurement but not more than 45 minutes. The stir motor's speed is set to 1200±50 rpm, corresponding to an indicated setting of 400±15 on the stepper motor controller. The barometric pressure surrounding the system, $P_{measured}$, is measured. The thickness (t) of the lens in the area being exposed for testing is determined by measuring about 10 locations with a Mitotoya micrometer VL-50, or similar instrument, and averaging the measurements. The oxygen concentration in the nitrogen stream (i.e., oxygen which diffuses through the lens) is measured using the DK1000 instrument. The apparent oxygen permeability of the lens material, $Dk_{app}$, is determined from the following formula:

$$Dk_{app}=Jt/(P_{oxygen})$$

where

J=oxygen flux [microliters O$_2$/cm$^2$-minute]

$P_{oxygen}=(P_{measured}-P_{water}$ vapor)=(% O$_2$ in air stream) [mm Hg]=partial pressure of oxygen in the air stream $P_{measured}$=barometric pressure (mm Hg)

$P_{water}$ vapor=0 mm Hg at about 35° C. (in a dry cell) (mm Hg)

$P_{water}$ vapor=40 mm Hg at about 35° C. (in a wet cell) (mm Hg)

t=average thickness of the lens over the exposed test area (mm)

$Dk_{app}$ is expressed in units of barrers.

The apparent oxygen transmissibility (Dk/t) of the material may be calculated by dividing the apparent oxygen permeability ($Dk_{app}$) by the average thickness (t) of the lens.

The above described measurements are not corrected for the so-called boundary layer effect which is attributable to the use of a water or saline bath on top of the contact lens during the oxygen flux measurement. The boundary layer effect causes the reported value for the apparent Dk of a silicone hydrogel material to be lower than the actual intrinsic Dk value. Further, the relative impact of the boundary layer effect is greater for thinner lenses than with thicker lenses. The net effect is that the reported Dk appear to change as a function of lens thickness when it should remain constant.

The intrinsic Dk value of a lens can be estimated based on a Dk value corrected for the surface resistance to oxygen flux caused by the boundary layer effect as follows.

Measure the apparent oxygen permeability values (single point) of the reference lotrafilcon A (Focus® N&D® from CIBA VISION CORPORATION) or lotrafilcon B (AirOptix™ from CIBA VISION CORPORATION) lenses using the same equipment. The reference lenses are of similar optical power as the test lenses and are measured concurrently with the test lenses.

Measure the oxygen flux through a thickness series of lotrafilcon A or lotrafilcon B (reference) lenses using the same equipment according to the procedure for apparent Dk measurements described above, to obtain the intrinsic Dk value ($Dk_i$) of the reference lens. A thickness series should cover a thickness range of approximately 100 μm or more. Preferably, the range of reference lens thicknesses will bracket the test lens thicknesses. The $Dk_{app}$ of these reference lenses must be measured on the same equipment as the test lenses and should ideally be measured contemporaneously with the test lenses. The equipment setup and measurement parameters should be held constant throughout the experiment. The individual samples may be measured multiple times if desired.

Determine the residual oxygen resistance value, $R_r$, from the reference lens results using equation 1 in the calculations.

$$R_r = \frac{\sum \left(\frac{t}{Dk_{app}} - \frac{t}{Dk_i}\right)}{n} \quad (1)$$

in which t is the thickness of the test lens (i.e., the reference lens too), and n is the number of the reference lenses measured. Plot the residual oxygen resistance value, $R_r$, vs. t data and fit a curve of the form Y=a+bX where, for the jth lens, $Y_j=(\Delta P/J)_j$ and $X=t_j$. The residual oxygen resistance, $R_r$ is equal to a.

Use the residual oxygen resistance value determined above to calculate the correct oxygen permeability $Dk_c$ (estimated intrinsic Dk) for the test lenses based on Equation 2.

$$Dk_c=t/[(t/Dk_a)-R_r] \quad (2)$$

The estimated intrinsic Dk of the test lens can be used to calculate what the apparent Dk ($Dk_{a\_std}$) would have been for a standard thickness lens in the same test environment based on Equation 3. The standard thickness ($t_{std}$) for lotrafilcon A=85 μm. The standard thickness for lotrafilcon B=60 μm.

$$Dk_{a\_std}=t_{std}/[(t_{std}/Dk_c)+R_{r\_std}] \quad (3)$$

Ion Permeability Measurements.

The ion permeability of a lens is measured according to procedures described in U.S. Pat. No. 5,760,100 (herein incorporated by reference in its entirety. The values of ion permeability reported in the following examples are relative ionoflux diffusion coefficients ($D/D_{ref}$) in reference to a lens material, Alsacon, as reference material. Alsacon has an ionoflux diffusion coefficient of 0.314×10$^{-3}$ mm$^2$/minute.

What is claimed is:

1. A carbosiloxane vinylic monomer of formula (I)

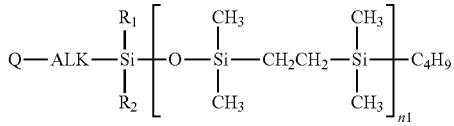

in which: n1 is an integer of 2 to 5; ALK is a $C_1$-$C_6$ alkyl diradical; $R_1$ and $R_2$ independent of each another are a $C_1$-$C_6$ alkyl radical; Q is an ethylenically unsaturated group selected from the group consisting of

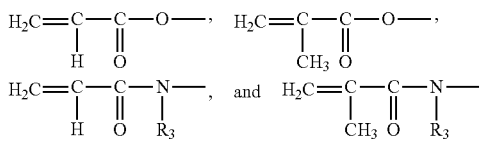

in which $R_3$ is hydrogen or a $C_1$-$C_6$ alkyl radical.

2. The carbosiloxane vinylic monomer of claim 1, wherein Q is an ethylenically unsaturated group of

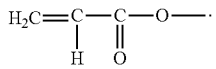

3. The carbosiloxane vinylic monomer of claim 1, wherein Q is an ethylenically unsaturated group of

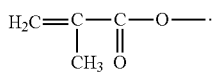

4. The carbosiloxane vinylic monomer of claim 1, wherein Q is an ethylenically unsaturated group of

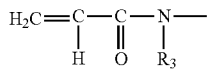

in which $R_3$ is hydrogen or a $C_1$-$C_6$ alkyl radical.

5. The carbosiloxane vinylic monomer of claim 1, wherein Q is an ethylenically unsaturated group of

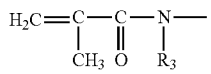

in which $R_3$ is hydrogen or a $C_1$-$C_6$ alkyl radical.

6. A polymer comprising monomeric units derived in a free-radical polymerization from a carbosiloxane vinylic monomer of claim 1.

7. The polymer of claim 6, wherein the polymer is an actinically-crosslinkable prepolymer having two or more ethylenically unsaturated groups.

8. The polymer of claim 7, wherein the actinically-crosslinkable prepolymer further comprises hydrophilic units derived in the free radical polymerization from at least one hydrophilic vinylic monomer.

9. The polymer of claim 6, wherein the polymer is a silicone hydrogel material which further comprises hydrophilic units derived in the free radical polymerization from at least one hydrophilic vinylic monomer.

10. A silicone hydrogel contact lens which is obtained by polymerizing a polymerizable composition comprising a carbosiloxane vinylic monomer of claim 1 and at least one hydrophilic vinylic monomer.

11. A silicone hydrogel contact lens which is obtained by polymerizing a polymerizable composition comprising an actinically-crosslinkable prepolymer of claim 8.

12. The silicone hydrogel contact lens of claim 10, wherein the contact lens has a water content of from about 20% to about 75% by weight when fully hydrated, an oxygen permeability (Dk) of at least about 40 barrers, and an elastic modulus of from about 0.1 MPa to about 2.0 MPa.

* * * * *